US00PP08102P

United States Patent [19]

Ilsink

[11] Patent Number: Plant 8,102

[45] Date of Patent: Jan. 19, 1993

[54] ROSE PLANT INTERPRINCE

[75] Inventor: Peter Ilsink, NE Leersum, Netherlands

[73] Assignee: Bear Creek Gardens, Inc., Medford, Oreg.

[21] Appl. No.: 715,452

[22] Filed: Jun. 14, 1991

[51] Int. Cl.[5] ..... A01H 5/00

[52] U.S. Cl. ..... Plt./23

[58] Field of Search ..... Plt. 23, 22, 14, 1

*Primary Examiner*—Howard J. Locker

*Attorney, Agent, or Firm*—Klarquist, Sparkman, Campbell, Leigh & Whinston

[57] ABSTRACT

A floribunda rose plant having the ability to produce, in the greenhouse, flowers borne in clusters that open simultaneously, high production of cut flowers in the greenhouse (180–200 per square meter), pure white flower color, vigorous upright growth, and good vase life.

1 Drawing Sheet

The present invention relates to a new and distinct variety of rose plant of the floribunda class which was originated by me by crossing the variety Pink Delight (no U.S. Patent), with an unnamed seedling.

The primary objective of this breeding was to produce a new rose variety having high production of simultaneously opening whitish blooms, preferably borne in clusters, with long vase life. The objective was substantially achieved along with other desirable improvements as evidenced by the following unique combination of characteristics which are outstanding in the new variety and which distinguish it from its parents, as well as from all other varities of which I am aware:

1. The ability to produce, in the greenhouse, flowers borne in clusters that open simultaneously.
2. High production of cut flowers in the greenhouse (about 180 to 200 blooms per square meter).
3. Pure white flower color.
4. Vigorous upright growth.
5. Good vase life.

Asexual reproduction of this new variety by budding, as performed at Wasco and Somis, Calif., shows that the foregoing characteristics and distinctions come true to form and are established and transmitted through succeeding propagations.

The accompanying color photograph shows typical specimens of the vegatative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Pink Delight.

*Pollen parent.*—Unnamed seedling.

Classification:

*Botanical.*—*Rosa hybrida.*

*Commercial.*—Floribunda.

FLOWER

Observations made from specimens grown in a greenhouse environment in Somis, Calif. in January, 1990, to February, 1991.

Blooming habit: Recurrent.

Bud:

*Size.*—1 inch when the petals start to unfurl.

*Form.*—Short, pointed ovoid.

*Color.*—When sepals first divide, bud color is White Group 155B. When half brown, the upper sides of the petals are White Group 155B; and the lower sides of the petals are White Group 155B.

*Sepals.*—Color: Green Group 138A. Surface texture: Covered with fine hairs. There are three lightly appendaged sepals. There are two unappendaged sepals with hairy edges and many glands.

*Receptacle.*—Color: Green Group 137D. Shape: Funnel. Size: Broad, small ($\frac{1}{2}$ inch $\times$ $\frac{3}{8}$ inch). Surface: Smooth.

*Peduncle.*—Length: Short ($2\frac{1}{4}$ inch to $2\frac{1}{2}$ inch). Surface: Smooth and glandular. Color: Light green. Strength: Stiff, erect.

Bloom:

*Size.*—Small. Average open size is $2\frac{3}{4}$ inches.

*Borne.*—Several together in flat to slightly rounded clusters.

*Stems.*—Medium to long (18 to 24 inches long).

*form.*—When first open: Has high center. Permanence: Bloom flattens; outer petals curl back with some quilling.

*Petalage.*—Number of petals under normal conditions: 30.

*Color.*—The upper side of the petals is White Group 155B. The reverse side of the petals is White Group 155B. The color of the base of petals intensifies to a very small greenish yellow area at the point of attachment at the petal base. The major color on the upper side is White Group 155B.

*Variegations.*—None.

*Discoloration.*—No change in general tonality at the end of the first day and no change at the end of the third day.

*Fragrance.*—Slight.

Petals:

*Texture.*—Thick.

*Shape.*—Round to slightly deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Long, 5 to 6 days. As a cut flower: Long, 7 to 8 days.

Reproductive parts:

*Anthers.*—Size: Medium. Quantity: Many. Color: Yellow. Arrangement: Regular around styles, mixed with occasional petaloids.

*Filaments.*—Color: Yellow.

*Pollen.*—Color: Gold yellow.

*Styles.*—Color: White.

*Stigmas.*—Color: White.

Form: Bush.

Growth: Very vigorous, upright, branching.

Foliage:

*Number of leaflets on normal mid-stem leaves.*—5 or 7.

*Size.*—Large (7 inches×5 inches).

*Quantity.*—Abundant.

*Color.*—New foliage: Green. Old foliage: Dark green, semi-glossy.

Leaflets:

*Shape.*—Broadly oval.

*Texture.*—Upper side: Smooth, semi-glossy.

*Edge.*—Serrated.

*Serration.*—Single, small.

*Petiole rachis.*—Color: Green.

*Petiole underside.*—Smooth with occasional prickles.

*Stipules.*—Medium, bearded.

*Disease resistance.*—Susceptible to mildew under normal growing conditions at Somis, Calif. This is a greenhouse variety and was not tested for blackspot or rust.

Wood:

*New wood.*—Color: Light green. Bark; Smooth.

*Old wood.*—Color: Green. Bark: Smooth.

Prickles:

*Quantity.*—Ordinary number on main canes from base and on laterals from main canes.

*Form.*—Medium, hooked slightly downward.

*Color when young.*—Red.

Small prickles:

*Quantity.*—None on main stalks or on laterals.

I claim:

1. A new and distinct variety of rose plant of the floribunda class, substantially as herein shown and described, characterized particularly as to novelty by the unique combination of its distinctive pure white color, its ability to produce flowers borne in clusters that open simultaneously, its vigorous upright growth, good vase life, and high cut flower production.

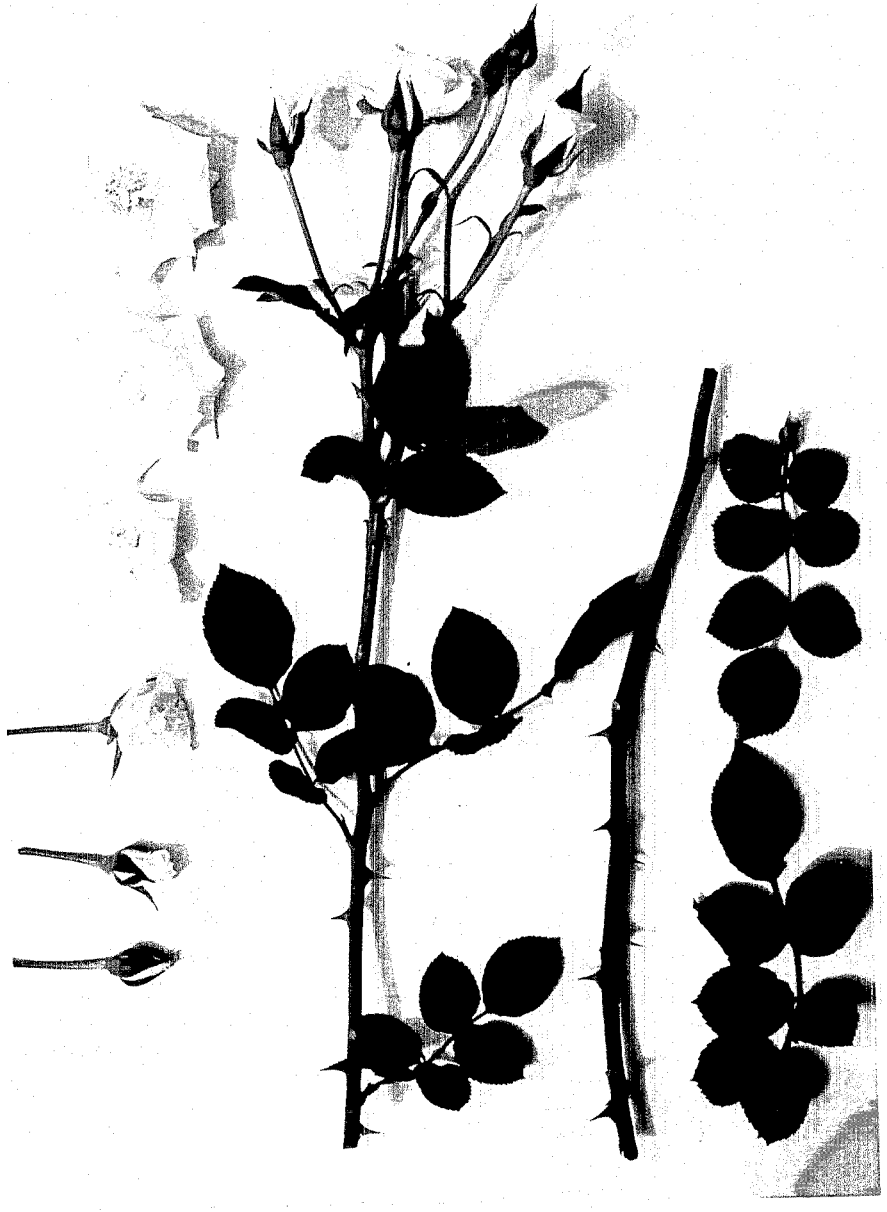

* * * * *